(12) United States Patent
Choi et al.

(10) Patent No.: US 10,947,542 B2
(45) Date of Patent: Mar. 16, 2021

(54) NUCLEIC ACID SIMULTANEOUSLY INHIBITING EXPRESSION OF AR GENE AND MTOR GENE

(71) Applicant: CURIGIN CO., LTD., Seoul (KR)

(72) Inventors: Jin-Woo Choi, Seoul (KR); Jung-Ki Yoo, Yangju-si (KR)

(73) Assignee: CURIGIN CO., LTD., Seoul (KR)

( * ) Notice: Subject to any disclaimer, the term of this patent is extended or adjusted under 35 U.S.C. 154(b) by 0 days.

(21) Appl. No.: 16/631,995

(22) PCT Filed: Jul. 19, 2018

(86) PCT No.: PCT/KR2018/008185
§ 371 (c)(1),
(2) Date: Jan. 17, 2020

(87) PCT Pub. No.: WO2019/017713
PCT Pub. Date: Jan. 24, 2019

(65) Prior Publication Data
US 2020/0231972 A1    Jul. 23, 2020

(30) Foreign Application Priority Data

Jul. 20, 2017 (KR) .................. 10-2017-0091951
Jul. 18, 2018 (KR) .................. 10-2018-0083461

(51) Int. Cl.
*C12N 15/113* (2010.01)
*C12N 15/85* (2006.01)

(52) U.S. Cl.
CPC .......... *C12N 15/1138* (2013.01); *C12N 15/85* (2013.01); *C12N 2310/14* (2013.01); *C12N 2310/531* (2013.01)

(58) Field of Classification Search
CPC ............... C12N 15/1138; C12N 15/85; C12N 2310/14; C12N 2310/531
See application file for complete search history.

(56) References Cited

U.S. PATENT DOCUMENTS

2005/0164970 A1   7/2005  Li
2018/0251762 A1*  9/2018  Peter ............... A61K 47/64

FOREIGN PATENT DOCUMENTS

KR   10-2009-0014673 A   2/2009
KR   10-1069101 B2       9/2011

OTHER PUBLICATIONS

Horvath et al (Nature Reviews Drug Discovery 15:751-769, Nov. 2016) (Year: 2016).*
Day et al (Cell 163: 39-53, 2015) (Year: 2015).*
Morgan (Mal. Ther. 20(5): 882-884, 2012) (Year: 2012).*
Du et al (Int J Clin Exp Pathol 7(3):923-931, 2014) (Year: 2014).*
Li et al (Nucl Acid Ther. 24(14): 302-312, 2014) (Year: 2014).*
Minoru Kato et al., "Co-targeting Androgen Receptor Splice Variants and mTOR signaling pathway for the Treatment of Castration-Resistant Prostate Cancer", Clin Cancer Res., Jun. 1, 2016, pp. 2744-2754, vol. 22, No. 11.
Yue Wu et al., "Androgen Receptor-mTOR Crosstalk is Regulated by Testosterone Availability: Implication for Prostate Cancer Cell Survival", Anticancer Research, 2010, pp. 3895-3902, vol. 30.
International Search Report for PCT/KR2018/008185 dated, Feb. 18, 2019 (PCT/ISA/210).

* cited by examiner

*Primary Examiner* — Richard A Schnizer
(74) *Attorney, Agent, or Firm* — Sughrue Mion, PLLC

(57) ABSTRACT

The present invention relates to nucleic acid molecules that simultaneously inhibit the expression of AR gene and mTOR gene, wherein the double-stranded siRNA and shRNA of the present invention were designed to simultaneously inhibit the expression of the AR gene and the mTOR gene which are associated with cancer. The double-stranded siRNA and shRNA of the present invention promote cancer cell death and synergistically enhance cancer cell death in combination with an anticancer agent, so that various types of cancer may be effectively prevented and treated.

10 Claims, 6 Drawing Sheets
Specification includes a Sequence Listing.

SEQUENCE LISTING

<160> NUMBER OF SEQ ID NOS: 41

<210> SEQ ID NO 1
<211> LENGTH: 20
<212> TYPE: RNA
<213> ORGANISM: Artificial Sequence
<220> FEATURE:
<223> OTHER INFORMATION: si-AT1_sense RNA (Antisense AR)

<400> SEQUENCE: 1
gcugcugcug cugccugggg                                          20

<210> SEQ ID NO 2
<211> LENGTH: 20
<212> TYPE: RNA
<213> ORGANISM: Artificial Sequence

```
<220> FEATURE:
<223> OTHER INFORMATION: si-AT1_antisense RNA (Antisense mTOR)

<400> SEQUENCE: 2
ccccaugcag cugcagcagc                                               20

<210> SEQ ID NO 3
<211> LENGTH: 19
<212> TYPE: RNA
<213> ORGANISM: Artificial Sequence
<220> FEATURE:
<223> OTHER INFORMATION: si-AT2_sense RNA (Antisense AR)

<400> SEQUENCE: 3
cugcugcugc ugccugggg                                                19

<210> SEQ ID NO 4
<211> LENGTH: 19
<212> TYPE: RNA
<213> ORGANISM: Artificial Sequence
<220> FEATURE:
<223> OTHER INFORMATION: si-AT2_antisense RNA (Antisense mTOR)

<400> SEQUENCE: 4
ccccaugcag cugcagcag                                                19

<210> SEQ ID NO 5
<211> LENGTH: 18
<212> TYPE: RNA
<213> ORGANISM: Artificial Sequence
<220> FEATURE:
<223> OTHER INFORMATION: si-AT3_sense RNA (Antisense AR)

<400> SEQUENCE: 5
ugcugcugcu gccugggg                                                 18

<210> SEQ ID NO 6
<211> LENGTH: 18
<212> TYPE: RNA
<213> ORGANISM: Artificial Sequence
<220> FEATURE:
<223> OTHER INFORMATION: si-AT3_antisense RNA (Antisense mTOR)

<400> SEQUENCE: 6
ccccaugcag cugcagca                                                 18

<210> SEQ ID NO 7
<211> LENGTH: 17
<212> TYPE: DNA
<213> ORGANISM: Artificial Sequence
<220> FEATURE:
<223> OTHER INFORMATION: si-AT4_sense RNA (Antisense AR)

<400> SEQUENCE: 7
gcugcugcug ccuggg                                                   17

<210> SEQ ID NO 8
<211> LENGTH: 17
<212> TYPE: RNA
<213> ORGANISM: Artificial Sequence
<220> FEATURE:
<223> OTHER INFORMATION: si-AT4_antisense RNA (Antisense mTOR)

<400> SEQUENCE: 8
ccccaugcag cugcagc                                                  17
```

```
<210> SEQ ID NO 9
<211> LENGTH: 19
<212> TYPE: RNA
<213> ORGANISM: Artificial Sequence
<220> FEATURE:
<223> OTHER INFORMATION: si-AT5_sense RNA (Antisense AR)

<400> SEQUENCE: 9
ccacccccac caccaccac                                              19

<210> SEQ ID NO 10
<211> LENGTH: 19
<212> TYPE: RNA
<213> ORGANISM: Artificial Sequence
<220> FEATURE:
<223> OTHER INFORMATION: si-AT5_antisense RNA (Antisense mTOR)

<400> SEQUENCE: 10
gugguggcag cgguggugg                                              19

<210> SEQ ID NO 11
<211> LENGTH: 18
<212> TYPE: RNA
<213> ORGANISM: Artificial Sequence
<220> FEATURE:
<223> OTHER INFORMATION: si-AT6_sense RNA (Antisense AR)

<400> SEQUENCE: 11
ccacccccac caccacca                                               18

<210> SEQ ID NO 12
<211> LENGTH: 18
<212> TYPE: RNA
<213> ORGANISM: Artificial Sequence
<220> FEATURE:
<223> OTHER INFORMATION: si-AT6_antisense RNA (Antisense mTOR)

<400> SEQUENCE: 12
ugguggcagc ggugguag                                               18

<210> SEQ ID NO 13
<211> LENGTH: 17
<212> TYPE: RNA
<213> ORGANISM: Artificial Sequence
<220> FEATURE:
<223> OTHER INFORMATION: si-AT7_sense RNA (Antisense AR)

<400> SEQUENCE: 13
ccacccccac caccacc                                                17

<210> SEQ ID NO 14
<211> LENGTH: 17
<212> TYPE: RNA
<213> ORGANISM: Artificial Sequence
<220> FEATURE:
<223> OTHER INFORMATION: si-AT7_antisense RNA (Antisense mTOR)

<400> SEQUENCE: 14
gguggcagcg guggugg                                                17

<210> SEQ ID NO 15
<211> LENGTH: 23
<212> TYPE: RNA
<213> ORGANISM: Artificial Sequence
<220> FEATURE:
<223> OTHER INFORMATION: si-AT8_sense RNA (Antisense AR)
```

```
<400> SEQUENCE: 15
uggaggcaga gagugagaga gaa                                              23

<210> SEQ ID NO 16
<211> LENGTH: 23
<212> TYPE: RNA
<213> ORGANISM: Artificial Sequence
<220> FEATURE:
<223> OTHER INFORMATION: si-AT8_antisense RNA (Antisense mTOR)

<400> SEQUENCE: 16
uucucucaga cgcucuccu cca                                               23

<210> SEQ ID NO 17
<211> LENGTH: 22
<212> TYPE: RNA
<213> ORGANISM: Artificial Sequence
<220> FEATURE:
<223> OTHER INFORMATION: si-AT9_sense RNA (Antisense AR)

<400> SEQUENCE: 17
ggaggcagag agugagagag aa                                               22

<210> SEQ ID NO 18
<211> LENGTH: 22
<212> TYPE: RNA
<213> ORGANISM: Artificial Sequence
<220> FEATURE:
<223> OTHER INFORMATION: si-AT9_antisense RNA (Antisense mTOR)

<400> SEQUENCE: 18
uucucucaga cgcucuccu cc                                                22

<210> SEQ ID NO 19
<211> LENGTH: 22
<212> TYPE: RNA
<213> ORGANISM: Artificial Sequence
<220> FEATURE:
<223> OTHER INFORMATION: si-AT10_sense RNA (Antisense AR)

<400> SEQUENCE: 19
uggaggcaga gagugagaga ga                                               22

<210> SEQ ID NO 20
<211> LENGTH: 22
<212> TYPE: RNA
<213> ORGANISM: Artificial Sequence
<220> FEATURE:
<223> OTHER INFORMATION: si-AT10_antisense RNA (Antisense mTOR)

<400> SEQUENCE: 20
ucucucagac gcucuccuc ca                                                22

<210> SEQ ID NO 21
<211> LENGTH: 21
<212> TYPE: RNA
<213> ORGANISM: Artificial Sequence
<220> FEATURE:
<223> OTHER INFORMATION: si-AT11_sense RNA (Antisense AR)

<400> SEQUENCE: 21
uggaggcaga gagugagaga g                                                21

<210> SEQ ID NO 22
```

```
<211> LENGTH: 21
<212> TYPE: RNA
<213> ORGANISM: Artificial Sequence
<220> FEATURE:
<223> OTHER INFORMATION: si-AT11_antisense RNA (Antisense mTOR)

<400> SEQUENCE: 22
cucucagacg cucucccucc a                                                 21

<210> SEQ ID NO 23
<211> LENGTH: 20
<212> TYPE: RNA
<213> ORGANISM: Artificial Sequence
<220> FEATURE:
<223> OTHER INFORMATION: si-AT12_sense RNA (Antisense AR)

<400> SEQUENCE: 23
ggaggcagag agugagagag                                                   20

<210> SEQ ID NO 24
<211> LENGTH: 20
<212> TYPE: RNA
<213> ORGANISM: Artificial Sequence
<220> FEATURE:
<223> OTHER INFORMATION: si-AT12_antisense RNA (Antisense mTOR)

<400> SEQUENCE: 24
cucucagacg cucucccucc                                                   20

<210> SEQ ID NO 25
<211> LENGTH: 21
<212> TYPE: RNA
<213> ORGANISM: Artificial Sequence
<220> FEATURE:
<223> OTHER INFORMATION: si-AT13_sense RNA (Antisense AR)

<400> SEQUENCE: 25
ggaggcagag agugagagag a                                                 21

<210> SEQ ID NO 26
<211> LENGTH: 21
<212> TYPE: RNA
<213> ORGANISM: Artificial Sequence
<220> FEATURE:
<223> OTHER INFORMATION: si-AT13_antisense RNA (Antisense mTOR)

<400> SEQUENCE: 26
ucucucagac gcucucccuc c                                                 21

<210> SEQ ID NO 27
<211> LENGTH: 20
<212> TYPE: DNA
<213> ORGANISM: Artificial Sequence
<220> FEATURE:
<223> OTHER INFORMATION: sense DNA (AR antisense)

<400> SEQUENCE: 27
gctgctgctg ctgcctgggg                                                   20

<210> SEQ ID NO 28
<211> LENGTH: 20
<212> TYPE: DNA
<213> ORGANISM: Artificial Sequence
<220> FEATURE:
<223> OTHER INFORMATION: antisense DNA (mTOR antisense)

<400> SEQUENCE: 28
```

```
ccccatgcag ctgcagcagc                                                    20

<210> SEQ ID NO 29
<211> LENGTH: 52
<212> TYPE: DNA
<213> ORGANISM: Artificial Sequence
<220> FEATURE:
<223> OTHER INFORMATION: TTCAAGAGAG loop shRNA

<400> SEQUENCE: 29
gctgctgctg ctgcctgggg ttcaagagag ccccatgcag ctgcagcagc tt               52

<210> SEQ ID NO 30
<211> LENGTH: 52
<212> TYPE: DNA
<213> ORGANISM: Artificial Sequence
<220> FEATURE:
<223> OTHER INFORMATION: TTGGATCCAA loop shRNA

<400> SEQUENCE: 30
gctgctgctg ctgcctgggg ttggatccaa ccccatgcag ctgcagcagc tt               52

<210> SEQ ID NO 31
<211> LENGTH: 276
<212> TYPE: DNA
<213> ORGANISM: Artificial Sequence
<220> FEATURE:
<223> OTHER INFORMATION: U7 promotor

<400> SEQUENCE: 31
cctagagtcg acactagata acaacatagg agctgtgatt ggctgttttc agccaatcag       60
cactgactca tttgcatagc ctttacaagc ggtcacaaac tcaagaaacg agcggtttta      120
atagtctttt agaatattgt ttatcgaacc gaataaggaa ctgtgctttg tgattcacat      180
atcagtggag gggtgtggaa atggcacctt gatctcaccc tcatcgaaag tggagttgat      240
gtccttccct ggctcgctac agacgcactt ccgcaa                                276

<210> SEQ ID NO 32
<211> LENGTH: 21
<212> TYPE: RNA
<213> ORGANISM: Artificial Sequence
<220> FEATURE:
<223> OTHER INFORMATION: AR siRNA sense strand
<220> FEATURE:
<221> NAME/KEY: modified base
<222> LOCATION: (20)
<223> OTHER INFORMATION: n = deoxythymidine
<220> FEATURE:
<221> NAME/KEY: modified base
<222> LOCATION: (21)
<223> OTHER INFORMATION: n = deoxythymidine

<400> SEQUENCE: 32
cacaaguccc ggauguacan n                                                 21

<210> SEQ ID NO 33
<211> LENGTH: 21
<212> TYPE: RNA
<213> ORGANISM: Artificial Sequence
<220> FEATURE:
<223> OTHER INFORMATION: AR siRNA antisense strand
<220> FEATURE:
<221> NAME/KEY: modified base
<222> LOCATION: (20)
<223> OTHER INFORMATION: n = deoxythymidine
<220> FEATURE:
```

```
<221> NAME/KEY: modified base
<222> LOCATION: (21)
<223> OTHER INFORMATION: n = deoxythymidine

<400> SEQUENCE: 33
uguacauccg ggacuugugn n                                      21

<210> SEQ ID NO 34
<211> LENGTH: 21
<212> TYPE: RNA
<213> ORGANISM: Artificial Sequence
<220> FEATURE:
<223> OTHER INFORMATION: mTOR siRNA sense strand
<220> FEATURE:
<221> NAME/KEY: modified base
<222> LOCATION: (20)
<223> OTHER INFORMATION: n = deoxythymidine
<220> FEATURE:
<221> NAME/KEY: modified base
<222> LOCATION: (21)
<223> OTHER INFORMATION: n = deoxythymidine

<400> SEQUENCE: 34
guggaaacag gacccaugan n                                      21

<210> SEQ ID NO 35
<211> LENGTH: 21
<212> TYPE: RNA
<213> ORGANISM: Artificial Sequence
<220> FEATURE:
<223> OTHER INFORMATION: mTOR siRNA antisense strand
<220> FEATURE:
<221> NAME/KEY: modified base
<222> LOCATION: (20)
<223> OTHER INFORMATION: n = deoxythymidine
<220> FEATURE:
<221> NAME/KEY: modified base
<222> LOCATION: (21)
<223> OTHER INFORMATION: n = deoxythymidine

<400> SEQUENCE: 35
ucaugggucc uguuuccacn n                                      21

<210> SEQ ID NO 36
<211> LENGTH: 19
<212> TYPE: DNA
<213> ORGANISM: Artificial Sequence
<220> FEATURE:
<223> OTHER INFORMATION: AR forward primer

<400> SEQUENCE: 36
ggaattcctg tgcatgaaa                                         19

<210> SEQ ID NO 37
<211> LENGTH: 19
<212> TYPE: DNA
<213> ORGANISM: Artificial Sequence
<220> FEATURE:
<223> OTHER INFORMATION: AR reverse primer

<400> SEQUENCE: 37
cgaagttcat caaagaatt                                         19

<210> SEQ ID NO 38
<211> LENGTH: 17
<212> TYPE: DNA
<213> ORGANISM: Artificial Sequence
<220> FEATURE:
<223> OTHER INFORMATION: mTOR forward primer
```

```
<400> SEQUENCE: 38
cgcgaacctc agggcaa                                                    17

<210> SEQ ID NO 39
<211> LENGTH: 20
<212> TYPE: DNA
<213> ORGANISM: Artificial Sequence
<220> FEATURE:
<223> OTHER INFORMATION: mTOR reverse primer

<400> SEQUENCE: 39
tcagcggtaa aagtgtcccc                                                 20

<210> SEQ ID NO 40
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 40
ctaggcgctc actgttctct c                                               21

<210> SEQ ID NO 41
<211> LENGTH: 17
<212> TYPE: DNA
<213> ORGANISM: Artificial Sequence
<220> FEATURE:
<223> OTHER INFORMATION: GAPDH reverse primer

<400> SEQUENCE: 41
gtccgagcgc tgacctt                                                    17
```

NUCLEIC ACID SIMULTANEOUSLY INHIBITING EXPRESSION OF AR GENE AND MTOR GENE

CROSS REFERENCE TO RELATED APPLICATIONS

This application is a National Stage of International Application No. PCT/KR2018/008185 filed Jul. 19, 2018, claiming priority based on Korean Patent Application No. 10-2017-0091951, filed Jul. 20, 2017 and Korean Patent Application No. 10-2018-0083461 filed Jul. 18, 2018, the entire disclosures of which are incorporated herein by reference.

TECHNICAL FIELD

The present disclosure relates to a nucleic acid molecule that simultaneously inhibits expression of AR and mTOR genes, and a pharmaceutical composition for anticancer containing the same.

BACKGROUND ART

Cancer is one of the world's most fatalities, and the development of innovative cancer treatment agents may reduce a cost of medical treatment of the cancer and create a high added value. Further, 2008 statistics show that a cost of a molecular treatment agent that might overcome existing anticancer-agent resistance amounted to $17.5 billion in seven major countries (US, Japan, France, Germany, Italy, Spain, UK). In 2018, a market size thereof is estimated to be about $45 billion and is expected to grow by 9.5% compared to 2008. Cancer treatment is divided into surgery, radiation therapy, chemotherapy, and biological therapy. Among them, chemotherapy inhibits or kills growth of cancer cells using a chemical substance. Toxicity induced by anticancer drugs significantly affects normal cells, resulting in some level of toxicity. Thus, although anticancer drugs achieve a desired effect, after a certain period of time, resistance to anticancer drugs develops. Thus, development of anticancer drugs that selectively act on cancer cells and do not have the resistance is urgently needed (Current situation of cancer conquest, Biowave 2004. 6 (19)). Recently, the development of new anticancer drugs targeting the molecular characteristics of cancer by securing molecular genetic information about the cancer is made. It has been reported that anticancer drugs targeting the characteristic molecular targets that only cancer cells have may not undergo the drug resistance.

Technology to inhibit the expression of genes is an important tool in the development of therapeutics for the treatment of diseases and in target validation. Since RNA interference (hereinafter, referred to as "RNAi") has been discovered, it has been found that the RNAi acts on sequence specific mRNA in various types of mammalian cells (Silence of the transcripts: RNA interference in medicine. J Mol Med (2005) 83:764773). The RNAi refers to a phenomenon in which small interfering RNA (hereinafter, referred to as "siRNA") with 21 to 25 nucleotide-sized double-helix structures specifically binds to a transcript (mRNA transcript) that has a complementary sequence and thereby degrades the transcript to inhibit the expression of a specific protein. In a cell, RNA double strand is processed by an endonuclease called Dicer and converted into siRNA of 21 to 23 double strands (base pair, bp). The siRNA binds to the RNA-induced silencing complex (RISC) and thus a guide (antisense) strand recognizes and degrades the target mRNA to inhibits the expression of the target gene in a sequence-specific manner (NUCLEIC-ACID THERAPEUTICS: BASIC PRINCIPLES AND RECENT APPLICATIONS. Nature Reviews Drug Discovery. 2002. 1, 503-514). According to Bertrand researchers, it has been reported that siRNAs for the same target genes are superior to antisense oligonucleotides (ASOs) in inhibiting mRNA expression in vitro and in vivo, and the effect thereof lasts for a long time (Comparison of antisense oligonucleotides and siRNAs in cell culture and in vivo. Biochem. Biophys. Res. Commun. 2002. 296:1000-1004). A market of the RNAi technology-based therapeutics including the siRNA is estimated to amount to more than 12 trillion won globally by 2020. An application target of this technology has been greatly expanded, and thus the RNAi technology-based therapeutics including the siRNA is being evaluated as the next generation gene therapy technology that may cure diseases that may not be treated with existing antibody and compound-based drugs. Further, because regarding the mechanism of action of siRNA, the siRNA binds to the target mRNA complementarily to regulate the expression of the target gene in a sequence specific manner, the application targets thereof may be significantly expanded and the development period thereof is shortened, thereby to develop ligand compounds optimized to all protein targets containing target substances which are not chemically produced (Progress Towards in Vivo Use of siRNAs. MOLECULAR THERAPY. 2006 13 (4):664-670). However, it requires a long development period and development cost that the existing antibody-based drugs or small molecule drugs are optimized to a specific protein target. Recently, this ribonucleic acid-mediated interference phenomenon suggests a solution to the problems arising from the development of conventional chemical synthetic drugs. Thus, this ribonucleic acid-mediated interference phenomenon selectively inhibits the expression of specific proteins at the transcript level. Thus, a research is underway to use the same in the development of various disease therapies, particularly tumor therapies. Further, unlike conventional anticancer drugs, the siRNA has the advantage that the target thereof is clear and thus side effects thereof are predictable. For a tumor as a disease caused by various gene problems, this target specificity may be a cause of the low therapeutic effect.

Androgen receptor (AR) refers to a kind of a nuclear receptor that is activated by binding any one of the androgen hormone, testosterone or dihydrotestosterone to the cytoplasm and then translocating the same to the nucleus (International Union of Pharmacology. LXV. The pharmacology and classification of the nuclear receptor superfamily: glucocorticoid, mineralocorticoid, progesterone, and androgen receptors. Pharmacological Reviews. 58 (4):782-97.). The AR mainly acts as DNA binding transcription factors that regulate gene expression (Biological actions of androgens. Endocrine Reviews. 8 (1):1-28.). Androgen receptors are modified by post-translational modifications via acetylation and are known to directly promote AR-mediated transactivation, apoptosis and contact independent growth of prostate cancer cells (Acetylation of androgen receptor enhances coactivator binding and promotes prostate cancer cell growth. Molecular and Cellular Biology. 23(23):8563-75). Further, androgen receptors are considered to be important in terms of therapeutic targets in prostate cancer. Thus, inhibitors targeting the N-terminal domain of proteins are being developed.

Meanwhile, mTOR (mammalian Target of rapamycin) is an important enzyme in a variety of signal transduction pathways including a cytokine-stimulated cell proliferation, translation of mRNA for several important proteins that regulate G1 phase of the cell cycle, and interleukin-2 (IL-2) induced transcription. Inhibition of mTOR causes inhibition of progression from G1 to S in the cell cycle. Since mTOR inhibitors exhibit immunoinhibitive, antiproliferative and anticancer activity, mTOR is targeted for the treatment of these diseases (Current Opinion in Lipidology, 16:317-323, 2005). Further, mTOR is an important factor in the regulation of autophagy. Targeting mTOR that regulates the autophagy pathways may treat a variety of diseases such as cancer, neurodegenerative diseases, heart disease, aging, immune diseases, infectious diseases and Crohn's disease (Immunology, 7:767-777 Nature 451:1069-1075, 2008).

Currently, because the mTOR exists in the cytoplasm, the existing antibody-based treatment agent that is widely used is not accessible to the mTOR. Further, systemic side effects may be problematic in the drug delivery of the mTOR. Thus, the present inventors have constructed siRNAs that are delivered topically and have excellent selectivity and thus are effective against carcinomas developed by AR and mTOR.

DISCLOSURE

Technical Problem

A purpose of the present disclosure is to overcome the disadvantage that the therapeutic effect due to the siRNA target specificity is not high. To this end, the present inventors prepared siRNA and shRNA which simultaneously inhibit the expression of AR gene and mTOR gene and identified anticancer activity thereof and synergistic anticancer activity thereof with anticancer agents. Thus, one purpose of the present disclosure is to use the prepared siRNA and shRNA effectively for cancer prevention and treatment.

Technical Solution

To achieve the above purpose, the present disclosure provides nucleic acid molecules that simultaneously inhibit the expression of AR and mTOR genes.

Further, the present disclosure provides a recombinant expression vector containing the nucleic acid molecule.

Further, the present disclosure provides transformed cells into which the recombinant expression vector has been introduced.

Further, the present disclosure provides a pharmaceutical composition for anticancer, the composition containing the nucleic acid molecule as an active ingredient.

Further, the present disclosure provides a method for prevention and treatment of cancer, the method including administering to a subject a pharmaceutically effective amount of the nucleic acid molecule.

Advantageous Effects

The present disclosure relates to nucleic acid molecules that simultaneously inhibit the expression of AR and mTOR genes. The double strand siRNA and shRNA according to the present disclosure were designed to simultaneously inhibit the expression of AR and mTOR genes related to cancer. The double strand siRNA and shRNA according to the present disclosure promote the death of cancer cells, and, when used in combination with an anticancer agent, realize an effect of synergistically improving cancer cell death therewith, so that various carcinomas may be effectively prevented and treated.

BEST MODES

Figure 1:
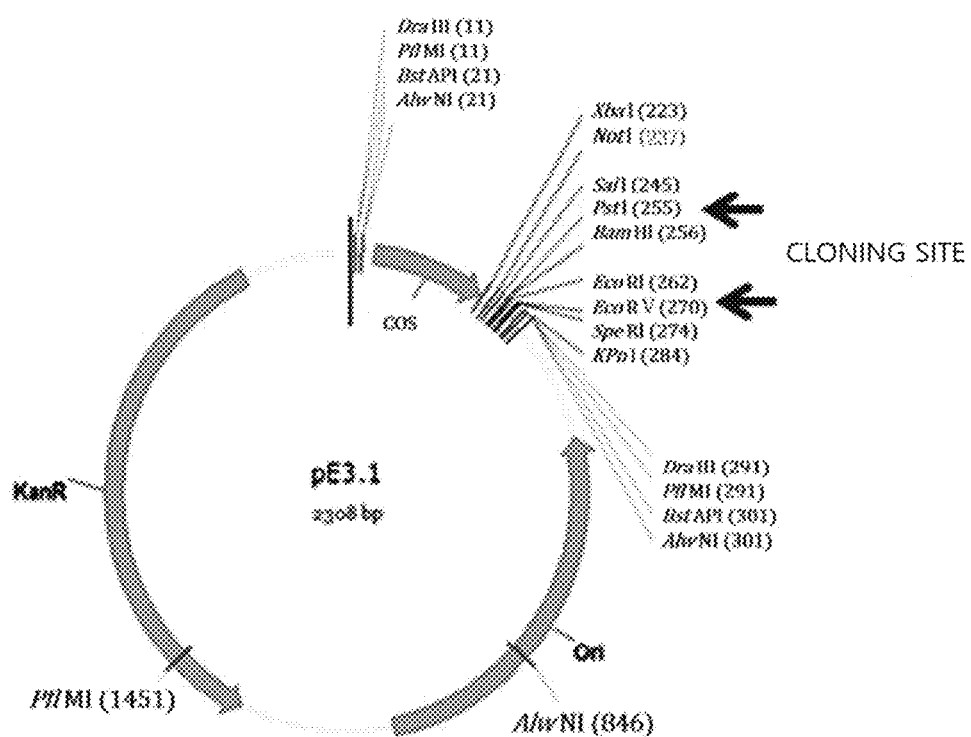
FIG. 1 shows a map of a vector for expressing shRNAs containing double target siRNA set 1 according to the present disclosure in cells.

Hereinafter, the present disclosure will be described in detail with reference to implementations according to the present disclosure. However, the following implementation is presented as an example of the present disclosure and does not limit the present disclosure. The present disclosure is subjected to various modifications and applications within a scope of following claims and equivalents to be interpreted therefrom.

In one aspect, the present disclosure relates to a nucleic acid molecule that simultaneously inhibits expression of AR and mTOR genes.

In one implementation, the nucleic acid molecule has a base sequence having 80% or greater sequence homology with at least one kind of base sequence selected from the group composed of the SEQ ID NOs: 1 and 2; SEQ ID NOs: 3 and 4; SEQ ID NOs: 5 and 6; SEQ ID NOs: 7 and 8; SEQ ID NOs: 9 and 10; SEQ ID NOs: 11 and 12; SEQ ID NOs: 13 and 14; SEQ ID NOs: 15 and 16; SEQ ID NOs: 17 and 18; SEQ ID NOs: 19 and 20; SEQ ID NOs: 21 and 22; SEQ ID NOs: 23 and 24; and SEQ ID NOs: 25 and 26.

In one implementation, the sequence homology is 81%, 82%, 83%, 84%, 85%, 86%, 87%, 88%, 89%, 90%, 91%, 92%, 93%, 94%, 95%, 96%, 97%, 98%, 99% or 100%.

In one implementation, the nucleic acid molecule having the base sequence represented by SEQ ID NO: 1, 3, 5, 7, 9, 11, 13, 15, 17, 19, 21, 23 or 25 may inhibit AR gene expression based on RNA interference. Further, the nucleic acid molecule having the base sequence represented by SEQ ID NO: 2, 4, 6, 8, 10, 12, 14, 16, 18, 20, 22, 24, or 26 may inhibit expression of the mTOR gene based on RNA interference. Thus, the nucleic acid molecule according to the present disclosure may simultaneously inhibit the expression of the AR and mTOR genes.

In one implementation, the nucleic acid molecule may be a double strand siRNA in which SEQ ID NO: 1 partially complementarily binds to SEQ ID NO: 2, SEQ ID NO: 3 partially complementarily binds to SEQ ID NO: 4, SEQ ID NO: 5 partially complementarily binds to SEQ ID NO: 6, SEQ ID NO: 7 partially complementarily binds to SEQ ID NO: 8, SEQ ID NO: 9 partially complementarily binds to SEQ ID NO: 10, SEQ ID NO: 11 partially complementarily binds to SEQ ID NO: 12, SEQ ID NO: 13 partially complementarily binds to SEQ ID NO: 14, SEQ ID NO: 15 partially complementarily binds to SEQ ID NO: 16, and SEQ ID NO: 17 partially complementarily binds to SEQ ID NO: 18, SEQ ID NO: 19 partially complementarily binds to SEQ ID NO: 20, SEQ ID NO: 21 partially complementarily binds to SEQ ID NO: 22, SEQ ID NO: 23 partially complementarily binds to SEQ ID NO: 24, or SEQ ID NO: 25 partially complementarily binds to SEQ ID NO: 26.

In one embodiment according to the present disclosure, siRNA sets 1 to 13 of a double target were prepared. Specifically, siRNA set 1 of 20mer composed of the SEQ ID NOs: 1 and 2 has a complementary binding length of 18mer therebetween. siRNA set 2 of 19mer composed of the SEQ ID NOs: 3 and 4 has a complementary binding length of 17mer therebetween. siRNA set 3 of 18mer composed of the SEQ ID NOs: 5 and 6 has a complementary binding length of 16mer therebetween. siRNA set 4 of 17mer composed of the SEQ ID NOs: 7 and 8 has a complementary binding length of 15mer therebetween. siRNA set 5 of 19mer composed of the SEQ ID NOs: 9 and 10 has a complementary binding length of 15mer therebetween. siRNA set 6 of 18mer composed of the SEQ ID NOs: 11 and 12 has a complementary binding length of 14mer therebetween. siRNA set 7 of 17mer composed of the SEQ ID NOs: 13 and 14 has a complementary binding length of 13mer therebetween. siRNA set 8 of 23mer composed of the SEQ ID NOs: 15 and 16 has a complementary binding length of 19mer therebetween. siRNA set 9 of 22mer composed of the SEQ ID NOs: 17 and 18 has a complementary binding length of 18mer therebetween. siRNA set 10 of 22mer composed of the SEQ ID NOs: 19 and 20 has a complementary binding length of 18mer therebetween. siRNA set 11 of 21mer composed of the SEQ ID NOs: 21 and 22 has a complementary binding length of 17mer therebetween. siRNA set 12 of 20mer composed of the SEQ ID NOs: 23 and 24 has a complementary binding length of 16mer therebetween. siRNA set 13 of 21mer composed of the SEQ ID NOs: 25 and 26 has a complementary binding length of 17mer therebetween.

In one embodiment according to the present disclosure, siRNA (antisense AR) of the SEQ ID NO: 1, 3, 5, 7, 9, 11, 13, 15, 17, 19, 21, 23 or 25 may complementarily bind to mRNA of AR. Further, siRNA (antisense mTOR) of SEQ ID NO: 2, 4, 6, 8, 10, 12, 14, 16, 18, 20, 22, 24 or 26 may bind complementarily to mRNA of mTOR. Therefore, the double target siRNA sets 1 to 13 according to the present disclosure may simultaneously reduce expression of AR and mTOR genes.

In one implementation, the nucleic acid molecule may be a short hairpin RNA (shRNA) having a base sequence represented by SEQ ID NO: 1 and a base sequence represented by SEQ ID NO: 2. The shRNA may have a sequence having 80% or greater sequence homology with the base sequence represented by SEQ ID NO: 29 or SEQ ID NO: 30.

In one implementation, the sequence homology may be 81%, 82%, 83%, 84%, 85%, 86%, 87%, 88%, 89%, 90%, 91%, 92%, 93%, 94%, 95%, 96%, 97%, 98%, 99% or 100%.

In one implementation, in the shRNA, the base sequence represented by SEQ ID NO: 1 and the base sequence represented by SEQ ID NO: 2 may partially complementary bind to each other and may be linked to each other via a loop region in a palindrome manner to form a hairpin structure. In one embodiment according to the present disclosure, the shRNA is expressed as TTCAAGAGAG loop shRNA (SEQ ID NO: 29) or TTGGATCCAA loop shRNA (SEQ ID NO: 30) according to a base sequence of the loop region of the hairpin structure.

In accordance with the present disclosure, siRNAs targeting AR and mTOR have a sequence complementary to a portion of AR or mTOR gene of human (Homo sapiens) and may degrade mRNA of AR gene or mTOR gene or may inhibit translation thereof.

As used herein, the term "inhibition of expression" means that the expression of the target gene (into mRNA) or translation (into protein) is degraded. Preferably, the inhibition of expression allows the target gene expression to be undetectable or to be present at a meaningless level.

As used herein, the term "small interfering RNA" (siRNA) refers to a short double-chain RNA that may induce RNA interference (RNAi) via cleavage of a specific mRNA. In general, siRNA is composed of a sense RNA strand having a sequence homologous to the mRNA of the target gene and an antisense RNA strand having a complementary sequence thereto. The double target siRNA according to the present disclosure is siRNA (antisense strand to AR gene) in which the sense RNA strand is composed of the base sequence represented by SEQ ID NO: 1, 3, 5, 7, 9, 11, 13, 15, 17, 19, 21, 23 or 25. The double target siRNA according to the present disclosure is siRNA (antisense strand to the mTOR gene) in which the antisense RNA strand is composed of the base sequence represented by SEQ ID NO: 2, 4, 6, 8, 10, 12, 14, 16, 18, 20, 22, 24 or 26. Thus, each of the double target siRNA sets 1 to 13 may inhibit the expression of the AR gene and the mTOR gene, and may be used for efficient gene knock-down method or for a gene therapy method.

The variant of the base sequence is included within the scope of the present disclosure. A variant of the nucleic acid molecule according to the present disclosure may be produced by modifying the nucleic acid molecule via deletion, substitution or insertion of some of base sequences of the functional equivalent to the nucleic acid molecule, for example, of the nucleic acid molecule that simultaneously inhibits the expression of the AR gene and mTOR gene. However, in terms of concept, the variant may be functionally equivalent to the nucleic acid molecule. Specifically, the variant may have a base sequence having at least 70%, more preferably at least 80%, even more preferably at least 90%, most preferably at least 95% homology with the base sequence represented by each of SEQ ID NOs as defined above. "% sequence homology" to a polynucleotide is identified by comparing a comparison region with two optimally arranged sequences. Some of the polynucleotide sequences in the comparison region may have an addition or deletion (i.e., gaps) of a reference sequence (not having addition or deletion) to the optimal arrangement of the two sequences.

In one aspect, the present disclosure relates to a recombinant expression vector containing a nucleic acid molecule according to the present disclosure.

In accordance with the present disclosure, the term "vector" is means of expressing a target gene in a host cell and includes a plasmid vector; phagemid vector; cosmid vector; and viral vectors such as bacteriophage vectors, adenovirus vectors, retrovirus vectors, and adeno-associated viral vectors, and the like. Preferably, the vector is an adeno-associated viral vector but is not limited thereto.

A vector according to the present disclosure may typically be constructed as a vector for cloning or a vector for expression. Further, the vector according to the present disclosure may be constructed using prokaryotic cell or eukaryotic cell as hosts. When the vector according to the present disclosure is an expression vector, and a prokaryotic cell is used as a host, the vector may contain powerful promoters capable of promoting transcription (e.g., tac promoter, lac promoter, lacUV5 promoter, lpp promoter, pL$\lambda$ promoter, pR$\lambda$ promoter, rac5 promoter, amp promoter, recA promoter, SP6 promoter, trp promoter and T7 promoter, etc.), ribosomal binding sites for initiation of translation, and transcription/translation termination sequences. When $E.$ $coli$ (e.g., HB101, BL21, DH5$\alpha$, etc.) is used as the host cell, promoter and operator regions of $E.$ $coli$ tryptophan biosynthetic pathway (Yanofsky, C. (1984), J. Bacteriol., 158: 1018-1024), and phage leftward promoter (pL$\lambda$ promoter, Herskowitz, I. and Hagen, D. 1980), Ann. Rev. Genet., 14:399-445) may be used as a regulatory region.

In one example, the vectors that may be used in the present disclosure may be prepared by manipulating plasmids (e.g. pSC101, pGV1106, pACYC177, ColE1, pKT230, pME290, pBR322, pUC8/9, pUC6, pBD9, pHC79, pIJ61, pLAFR1, pHV14, pGEX series, pET series and pUC19, etc.), phagemid (e.g. pComb3X), phage (M13, etc.) or virus (e.g. SV40, etc.) as often used in the art.

In one example, when the vector according to the present disclosure is an expression vector, and eukaryotic cells are used as hosts, promoters (e.g., metallothionine promoters) derived from the genome of mammalian cells, or promoters (e.g., late adenovirus promoters, vaccinia virus 7.5K promoters, SV40 promoters, cytomegalovirus promoters and HSV-TK promoters) derived from mammalian viruses may be used. The vector generally has a polyadenylation sequence as a transcription termination sequence.

Vectors according to the present disclosure may be fused with other sequences as needed to facilitate protein purification of amino acids. As the sequence to be fused, for example, glutathione S-transferase (Pharmacia, USA), maltose binding protein (NEB, USA), FLAG (IBI, USA) and 6×His (hexahistidine; Quiagen, USA) may be used. However, the present disclosure is not limited thereto. Further, the expression vector according to the present disclosure may contain antibiotic resistance genes commonly used in the art as a selection marker. For example, the expression vector has resistance genes to ampicillin, gentamicin, carbenicillin, chloramphenicol, streptomycin, kanamycin, geneticin, neomycin and tetracycline.

In one implementation, the recombinant expression vector according to the present disclosure may contain siRNA containing a base sequence represented by SEQ ID NO: 1 and siRNA containing a base sequence represented by SEQ ID NO: 2. the recombinant expression vector according to the present disclosure may contain shRNA having the base sequence represented by SEQ ID NO: 29 or shRNA having the base sequence of the base sequence represented by SEQ ID NO: 30.

The recombinant vectors according to the present disclosure may be produced by recombinant DNA methods known in the art. In one embodiment, the pE3.1 vector was used in the production method.

In accordance with the present disclosure, non-viral vectors useful for delivering siRNAs to AR and mTOR typically include all the vectors used for gene therapy, for example, various plasmids and liposomes that may be expressed in eukaryotic cells.

In accordance with present disclosure, in order to ensure that double strand siRNAs targeting AR and mTOR are properly transcribed in the cells receiving the same, preferably, the shRNA containing the same, in particular, a shRNA composed of a base sequence represented by SEQ ID NO: 29 or a base sequence represented by SEQ ID NO: 30 is operably linked to at least a promoter. The promoter may be any promoter as long as the promoter is capable of functioning in eukaryotic cells. The U7 promoter set forth as SEQ ID NO: 31 is more preferable. For efficient transcription of double strand siRNA or shRNA targeting AR and mTOR, if necessary, the vector may further contain a regulatory sequence including a leader sequence, a polyadenylation sequence, a promoter, an enhancer, an upstream activation sequence, a signal peptide sequence, and a transcription terminator factor.

In accordance with the present disclosure, viruses or viral vectors useful for delivering siRNA or shRNA related to AR and mTOR include baculoviridiae, parvoviridiae, picornoviridiae, herpesviridiae, poxviridiae, adenoviridiae, and the like, but are not limited thereto.

In one aspect, the present disclosure is directed to an anticancer pharmaceutical composition containing a nucleic acid molecule according to the present disclosure as an active ingredient.

In one implementation, the anticancer pharmaceutical composition according to the present disclosure may further contain an anticancer agent. The anticancer agents may include at least one kind selected from the group consisting of acibaicin, aclarubicin, acodazole, acronycin, adozelesin, alanosine, aldesleukin allopurinol sodium, altretamine, aminoglutetidemide, amonaphide, ampligen, amsacrine, androgens, anguidine, apidicholine glycinate, asaray, asparaginase, 5-azacytidine, azathioprine, bacillus calmethe-guerin (BCG), bakers antipol, beta-2-dioxythioguanosine, bisanthrene HCl, bleomycin sulfate, busulfan, buthionine sulfoximine, BWA 773U82, BW 502U83/HCl, BW 7U85 mesylate, cerasemide, carbetimer, carboplatin, carmustine, chlorambucil, chloroquinoxaline-sulfonamide, chlorozotocin, chromomycin A3, cisplatin, cladribine, corticosteroids, corynebacterium parboom, CPT-11, crisnatol, cyclocytidine, cyclophosphamide, cytarabine, cytembena, dabis maleate, dacarbazine, dactinomycin, daunorubicin HCl, diazaziridine, dexlazoic acid, dianhydrogalactitol, diajicuone, dibromodulcitol, dididemin B, diethyldithiocarbamate, diglycoaldehyde, dihydro-5-azacytin, doxorubicin, echinomycin, dedatrexate, edelfosine, epronitine, elliots solution, elsammitrusin, epirubicin, esorubicin, estramastine phosphate, estrogen, ethanidazole, ethiophos, etoposide, padrazole, pazarabine, fenretinide, filgrastim, finasteride, flavone acetic acid, floxuridine, fludarabine phosphate, 5'-fluorouracil, Fluosol, flutamide, gallium nitrate, gemcitabine, goserelin acetate, hepsulpam, hexamethylene bisacetamide, homoharringtonine, hydrazine sulfate, 4-hydroxyandrostenedione, hydroziurea, idarubicin HCl, ifosfamide, 4-ipomeanol, iproplatin, isotretinoin, leucovorin calcium, leuprolide acetate, levamisole, liposome daunorubicin, liposome capture doxorubicin, romastin, ronidamin, maytansine, mechlorethamine hydrochloride, melphalan, menogaryl, merbaron, 6-mercaptopurine, mesna, methanol extract of Bacillus calete-guerin, methotrexate, N-methylformamide, mifepristone, mitoguazone, mitomycin-C, mitotane, mitoxantrone hydrochloride, monocyte/macrophage colony-stimulating factor, nabilone, napoxidine, neocarzinostatin, octreotide acetate, ormaplatin, oxaliplatin, paclitaxel, pala, pentostatin, piperazinedione, pipeobroman, pirarubicin, pyretrexime, pyroxanthrone hydrochloride, PIXY-321, plicamycin, porfimer sodium, prednismustine, procarbazine, progestins, pyrazopurin, lazoic acid, sargramostim, semusstin, spirogermanium, spiromostin, streptonaigreen, streptozosin, sulofener, suramin sodium, tamoxifen, taxorere, tegapur, teniposide, terephthalamidine, thyroxine, thioguanine, thiotepa, thymidine injection, tiazofurine, topotecan, toremifene, tretinoin, trifluoperazine hydrochloride, trifluridine, trimetrexate, tumor necrosis factor (TNF), uracil mustard, vinblastine sulfate, vincristine sulfate, binderesin, vinorelbine, vinzolidine, Yoshi 864, zorubicin, cytosine arabinoside, etoposide, and melphalan and taxol. Preferably, the anticancer agent may be taxol, cisplatin or etoposide. However, as long as the anticancer agent achieves the purpose of synergistic effect in combination with the double target siRNA set according to the present disclosure, the present disclosure is not limited thereto.

In one implementation, the cancer may be one selected from the group consisting of colon cancer, breast cancer, uterine cancer, cervical cancer, ovarian cancer, prostate cancer, brain tumors, head and neck cancers, melanoma, myeloma, leukemia, lymphoma, gastric cancer, lung cancer, pancreatic cancer, non-small cell lung cancer, liver cancer, esophageal cancer, small intestine cancer, anal muscle cancer, fallopian tube carcinoma, endometrial carcinoma, vaginal carcinoma, vulvar carcinoma, Hodgkin's disease, bladder cancer, kidney cancer, ureter cancer, renal cell carcinoma, renal pelvis carcinoma, bone cancer, skin cancer, head cancer, neck cancer, skin melanoma, intraocular melanoma, endocrine gland cancer, thyroid cancer, parathyroid cancer, adrenal cancer, soft tissue sarcoma, urethral cancer, penile cancer, central nervous system (CNS) tumor, primary CNS lymphoma, spinal cord tumor, glioblastoma multiforme and pituitary adenoma. The cancer may be prostate cancer or lung cancer in a more preferred example. However, the present disclosure is not limited thereto as long as the cancer may be treated with the double target siRNA set according to the present disclosure.

The term "treatment" as used in the present disclosure means any action that improves cancer cell death or beneficially alters cancer by administration of a composition containing the nucleic acid according to the present disclosure. A person having ordinary knowledge in the technical field to which the present disclosure belongs may refer to the data presented by the Korean Medical Association, etc. to know the exact criteria for the disease to which the composition according to the present disclosure is effective and to determine the extent of improvement, and treatment.

In one implementation, the pharmaceutical composition may be at least one formulation selected from the group containing oral formulations, external preparations, suppositories, sterile injectable solutions and sprays.

The therapeutically effective amount of the composition according to the present disclosure may vary depending on several factors, for example, the method of administration, the target region, and the condition of the patient. Therefore, when the composition is used in humans, the dosage thereof should be determined in an appropriate amount in consideration of both safety and efficiency. It is possible to estimate the amount to be used in humans from the effective amount determined based on the animal testing. The considerations used in determining the effective amount may be described, for example, in Hardman and Limbird, eds., Goodman and Gilman's The Pharmacological Basis of Therapeutics, 10th ed. (2001), Pergamon Press; And E. W. Martin ed., Remington's Pharmaceutical Sciences, 18th ed. (1990), Mack Publishing Co.

The composition according to the present disclosure may further contain carriers, diluents, excipients or combinations of two or more thereof commonly used in biological agents. Pharmaceutically acceptable carriers are not particularly limited so long as the composition containing the same is suitable for in vivo delivery. For example, compounds set forth in Merck Index, 13th ed., Merck & Co. Inc., saline, sterile water, Ringer's solution, buffered saline, dextrose solution, maltodextrin solution, glycerol, ethanol and a mixture of at least one of these components may be used. If necessary, other conventional additives such as antioxidants, buffers, bacteriostatic agents, and the like may be added to the composition. Further, diluents, dispersants, surfactants, binding agents and lubricants may be additionally added thereto to formulate the composition into injectable forms such as aqueous solutions, suspensions, emulsions and the like, and pills, capsules, granules or tablets. Furthermore, the composition may be preferably formulated according to each disease or component by a suitable method in the art or using a method disclosed in Remington's Pharmaceutical Science (Mack Publishing Company, Easton Pa., 18th, 1990).

The composition according to the present disclosure may further contain at least one kind of active ingredient exhibiting the same or similar functions. The composition according to the present disclosure contains 0.0001 to 10% by weight of the ingredient, preferably 0.001 to 1% by weight thereof, based on the total weight of the composition.

The pharmaceutical composition according to the present disclosure may further contain a pharmaceutically acceptable additive. Pharmaceutically acceptable additives may include starch, gelatinized starch, microcrystalline cellulose, lactose, povidone, colloidal silicon dioxide, calcium hydrogen phosphate, lactose, mannitol, syrup, gum Arabic, pregelatinized starch, corn starch, powdered cellulose, hydroxypropyl cellulose, opadry, sodium starch glycolate, lead carnauba, synthetic aluminum silicate, stearic acid, magnesium stearate, aluminum stearate, calcium stearate, sucrose, dextrose, sorbitol, talc, and the like. The pharmaceutically acceptable additive according to the present disclosure is preferably contained in an amount of 0.1 to 90 parts by weight based on the composition but is not limited thereto.

The composition according to the present disclosure may be administered non-orally (e.g., intravenously, subcutaneously, intraperitoneally or topically) or orally, depending on the desired method. The dosage may vary depending on the patient's weight, age, sex, health condition, diet, time of administration, method of administration, rate of excretion and severity of disease. The daily dose of the composition according to the present disclosure may be 0.0001 to 10 mg/ml, preferably 0.0001 to 5 mg/ml. More preferably, the composition may be administered once or several times a day in a divided manner.

Liquid preparations for oral administration of the composition according to the present disclosure may include suspensions, solvents, emulsions, and syrups. In addition to commonly used simple diluents such as water and liquid paraffin, the preparation may contain a variety of excipients, such as wetting agents, sweeteners, fragrances, and preservatives. Preparations for parenteral administration include sterile aqueous solutions, non-aqueous solvents, suspensions, emulsions, lyophilized preparations, suppositories, and the like.

The pharmaceutical composition according to the present disclosure may be used to prevent or treat cancer and its complications and may be used as an anticancer supplement.

Further, the present disclosure provides a method for the prevention and treatment of cancer, the method including administering to a subject a pharmaceutically effective amount of the nucleic acid molecule.

The pharmaceutical composition according to the present disclosure is administered in a therapeutically effective amount or in a pharmaceutically effective amount. The term "pharmaceutically effective amount" means an amount sufficient to treat a disease at a reasonable benefit/risk ratio applicable to medical treatment. Effective dose levels may be determined based on factors such as the disease type and severity of the individual, age, sex, activity of the drug, sensitivity to the drug, time of administration, route of administration and rate of release, duration of treatment, concurrently used drugs, and other well-known factors in the medical field.

The present disclosure will be described in more detail through the Example below. However, the following Example is intended to materialize the content according to the present disclosure, thereby not limiting the present disclosure.

MODES

Example 1. Double Target siRNA Preparation

Sets of double target siRNAs (double strands) that may simultaneously inhibit AR (androgen receptor) and mTOR (mammalian target of rapamycin) were prepared to have the sequences listed in Table 1 (Bioneer, Daej eon, Korea).

TABLE 1

| set | siRNA | Sequence(sense), 5'-3' | SEQ ID No | Sequence (antisense), 5'-3' | SEQ ID NO. | length | Complementary Binding Length |
|---|---|---|---|---|---|---|---|
| 1 | Si-AT1 | GCU GCU GCU GCU GCC UGG GG | 1 | CCC CAU GCA GCU GCA GCA GC | 2 | 20mer | 18mer |
| 2 | si-AT2 | CUG CUG CUG CUG CCU GGG G | 3 | CCC CAU GCA GCU GCA GCA G | 4 | 19mer | 17mer |
| 3 | si-AT3 | UGC UGC UGC UGC CUG GGG | 5 | CCC CAU GCA GCU GCA GCA | 6 | 18mer | 16mer |
| 4 | si-AT4 | GCU GCU GCU GCC UGG GG | 7 | CCC CAU GCA GCU GCA GC | 8 | 17mer | 15mer |
| 5 | si-AT5 | CCA CCC CCA CCA CCA CCA C | 9 | GUG GUG GCA GCG GUG GUG G | 10 | 19mer | 15mer |
| 6 | si-AT6 | CCA CCC CCA CCA CCA CCA | 11 | UGG UGG CAG CGG UGG UGG | 12 | 18mer | 14mer |
| 7 | si-AT7 | CCA CCC CCA CCA CCA CC | 13 | GGU GGC AGC GGU GGU GG | 14 | 17mer | 13mer |
| 8 | si-AT8 | UGG AGG CAG AGA GUG AGA GAG AA | 15 | UUC UCU CAG ACG CUC UCC CUC CA | 16 | 23mer | 19mer |
| 9 | si-AT8 | GGA GGC AGA GAG UGA GAG AGA A | 17 | UUC UCU CAG ACG CUC UCC CUC C | 18 | 22mer | 18mer |
| 10 | si-AT10 | UGG AGG CAG AGA GUG AGA GAG A | 19 | UCU CUC AGA CGC UCU CCC UCC A | 20 | 22mer | 18mer |
| 11 | si-AT11 | UGG AGG CAG AGA GUG AGA GAG | 21 | CUC UCA GAC GCU CUC CCU CCA | 22 | 21mer | 17mer |
| 12 | si-AT12 | GGA GGC AGA GAG UGA GAG AG | 23 | CUC UCA GAC GCU CUC CCU CC | 24 | 20mer | 16mer |
| 13 | si-AT13 | GGA GGC AGA GAG UGA GAG AGA | 25 | UCU CUC AGA CGC UCU CCC UCC | 26 | 21mer | 17mer | siRNA set 1 of 20mer composed of the SEQ ID NOs: 1 and 2 has a complementary binding length of 18mer therebetween. siRNA set 2 of 19mer composed of the SEQ ID NOs: 3 and 4 has a complementary binding length of 17mer therebetween. siRNA set 3 of 18mer composed of the SEQ ID NOs: 5 and 6 has a complementary binding length of 16mer therebetween. siRNA set 4 of 17mer composed of the SEQ ID NOs: 7 and 8 has a complementary binding length of 15mer therebetween. siRNA set 5 of 19mer composed of the SEQ ID NOs: 9 and 10 has a complementary binding length of 15mer therebetween. siRNA set 6 of 18mer composed of the SEQ ID NOs: 11 and 12 has a complementary binding length of 14mer therebetween. siRNA set 7 of 17mer composed of the SEQ ID NOs: 13 and 14 has a complementary binding length of 13mer therebetween. siRNA set 8 of 23mer composed of the SEQ ID NOs: 15 and 16 has a complementary binding length of 19mer therebetween. siRNA set 9 of 22mer composed of the SEQ ID NOs: 17 and 18 has a complementary binding length of 18mer therebetween. siRNA set 10 of 22mer composed of the SEQ ID NOs: 19 and 20 has a complementary binding length of 18mer therebetween. siRNA set 11 of 21mer composed of the SEQ ID NOs: 21 and 22 has a complementary binding length of 17mer therebetween. siRNA set 12 of 20mer composed of the SEQ ID NOs: 23 and 24 has a complementary binding length of 16mer therebetween. siRNA set 13 of 21mer composed of the SEQ ID NOs: 25 and 26 has a complementary binding length of 17mer therebetween.

The siRNA (antisense AR) of the SEQ ID NO: 1, 3, 5, 7, 9, 11, 13, 15, 17, 19, 21, 23 or 25 binds complementarily to mRNA of AR. siRNA (antisense mTOR) of SEQ ID NO: 2, 4, 6, 8, 10, 12, 14, 16, 18, 20, 22, 24 or 26 binds complementarily to mRNA of mTOR. Therefore, siRNA sets 1 to 13 according to the present disclosure simultaneously reduce expression of AR and mTOR genes.

Example 2. Double Target shRNA Preparation

In order to be able to express the double target siRNA prepared in the Example 1 in cells, shRNAs (TT-CAAGAGAG loop shRNA and TTGGATCCAA loop shRNA) containing DNA conversion sequences (SEQ ID NOs: 27 and 28) of the double target siRNA set 1 (si-AT 1) and the loop sequence thereof were prepared (Table 2). The prepared shRNAs were placed in a subsequent position to the U7 promoter (SEQ ID NO: 31) and at the restriction enzymes PstI and EcoRV cleavage sites of the pE3.1 vector (FIG. 1), respectively. Thus, a recombinant expression vector capable of expressing two kinds of shRNAs containing the double target siRNAs targeting AR and mTOR in cells was prepared.

TABLE 2

| | Sequence (5'→3') | SEQ ID NO. |
|---|---|---|
| Antisense AR | GCTGCTGCTGCTGCCTGGGG | 27 |
| Antisence mTOR | CCCCATGCAGCTGCAGCAGC | 28 |
| TTCAAGAGAG loop shRnA | GCTGCTGCTGCTGCCTGGGGTTCAAGAG AGCCCCATGCAGCTGCAGCAGCTT | 29 |
| TTGGATCCAA loop shRNA | GCTGCTGCTGCTGCCTGGGGTTGGATCCA ACCCCATGCAGCTGCAGCAGCTT | 30 |

Experimental Example 1. Identification of AR Gene and mTOR Gene Expression Inhibition Effect by Double Target siRNA Sets 1 to 13

1-1. Identification of Inhibitory Effect of AR Gene and mTOR Gene Expression by Double Target siRNA Set 1 (Si-AT1)

We dispensed PC3 and h460 cell lines into 12-well plates, and incubated the same at 37° C. and 5% $CO_2$ condition in RPMI medium (Hyclone company) with 10% FBS (Hyclone company) until a cell confluent reaches 50%. Thereafter, 3 μl of lipofectamine 3000 (Invitrogen, Carlsbad, Calif., USA) was used to transfect the double target siRNA set 1 prepared in the Example 1 (si-AT 1) to the wells in which the cells were cultured at 80 pmole per well. Thus, AR and mTOR were knocked down simultaneously. In addition, siRNA to AR and siRNA to mTOR were transfected respectively, as listed in the following table 3, as a positive control. At 48 hours after the transfection, cells were crushed, and total RNA was extracted using GeneJET RNA Purification Kit (Invitrogen). While using the extracted total RNA as a template, the same was subjected to reverse transcription into cDNA via RT-PCR reaction. Then, mRNA expression levels of AR and mTOR by each siRNA and by the double target siRNA set 1 (si-AT1) according to the present disclosure was identified via q-PCR reaction. To identify the mRNA expression levels, the mRNA of AR and mTOR in the cell lysates knocked down by PCR conditions of Table 6 was converted to cDNA using the primer set from Table 4 and the reaction mixture from Table 5. Further, while using the reverse-transcribed cDNA as a template, the reaction mixture was prepared with the composition of Table 7 below. Then, qPCR was performed under the conditions of Table 8. For reference, the probes used were AR (Thermo, Hs00171172_m1), mTOR (Thermo, Hs00234508_m1), GAPDH (Thermo, Hs02786624_g1). The PCR was done using QS3 equipment. All reactions were repeated three times and then, mean values thereof were taken. The results as obtained were normalized relative to the mRNA value of GAPDH as a housekeeping gene.

TABLE 3

| | | Sequence (5'→3') | SEQ ID NO |
|---|---|---|---|
| AR siRNA | sense | CACAAGUCCCGGAUGUACA(dTdT) | 32 |
| | antisense | UGUACAUCCGGGACUUGUG(dTdT) | 33 |
| mTOR siRNA | sense | GUGGAAACAGGACCCAUGA(dTdT) | 34 |
| | antisense | UCAUGGGUCCUGUUUCCAC(dTdT) | 35 |

TABLE 4

| | | Sequence (5'→3') | SEQ ID NO. |
|---|---|---|---|
| AR | forward | GGAATTCCTGTGCATGAAA | 36 |
| | reverse | CGAAGTTCATCAAAGAATT | 37 |
| mTOR | forward | CGCGAACCTCAGGGCAA | 38 |
| | reverse | TCAGCGGTAAAAGTGTCCCC | 39 |
| GAPDH | forward | CTAGGCGCTCACTGTTCTCTC | 40 |
| | reverse | GTCCGAGCGCTGACCTT | 41 |

TABLE 5

| 10X reaction Buffer | 2 μℓ |
|---|---|
| HQ Buffer | 2 μℓ |
| dNTP | 1.6 μℓ |
| Primer (F, R, 10 pmole/ul) | Each 1 μℓ |
| Template (500 ng) | 2 μℓ |

TABLE 5-continued

| Taq | 0.2 μℓ |
|---|---|
| DW | 10.2 μℓ |
| Total vol. | 20 μℓ |

TABLE 6

| Pre heat 95° C. | 2 min | |
|---|---|---|
| Denaturation 95° C. | 20 sec | 30 cycles |
| Annealing 60° C. | 10 sec | |
| Extension 72° C. | 30~60 sec | |
| Final extension 72° C. | 5 min | |

TABLE 7

| Template(RT-PCR product) | 6 μℓ |
|---|---|
| Taqman probe | 3 μℓ |
| 10X reaction Buffer | 6 μℓ |
| HQ Buffer | 6 μℓ |
| dNTP | 4.8 μℓ |
| Taq | 0.6 μℓ |
| DW | 10.2 μℓ |
| Total vol. | 60 μℓ |

TABLE 8

| Pre denaturation 95° C. | 10 min | |
|---|---|---|
| Denaturation 95° C. | 15 sec | 40 cycles |
| Extension 60° C. | 1 min | |

Figure 2A:
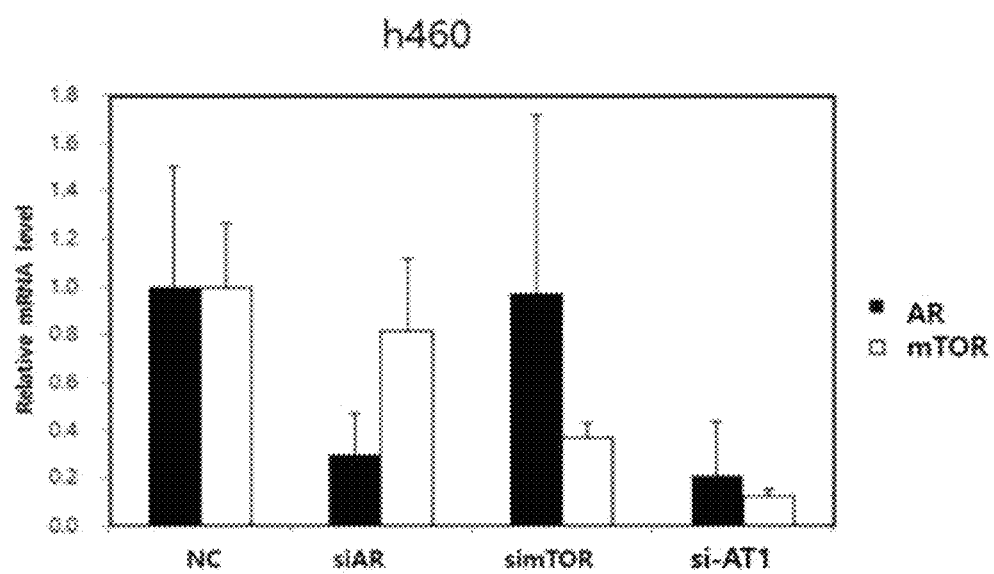
FIG. 2A is a diagram identifying inhibitory effects of AR gene and mTOR gene expression by the double target siRNA set 1 according to the present disclosure on h460 cell line (NC is control siRNA, siAR is siRNA for AR, simTOR is siRNA for mTOR, si-AT1 is AR and mTOR double target siRNA set 1 according to the present disclosure).
Figure 2B:
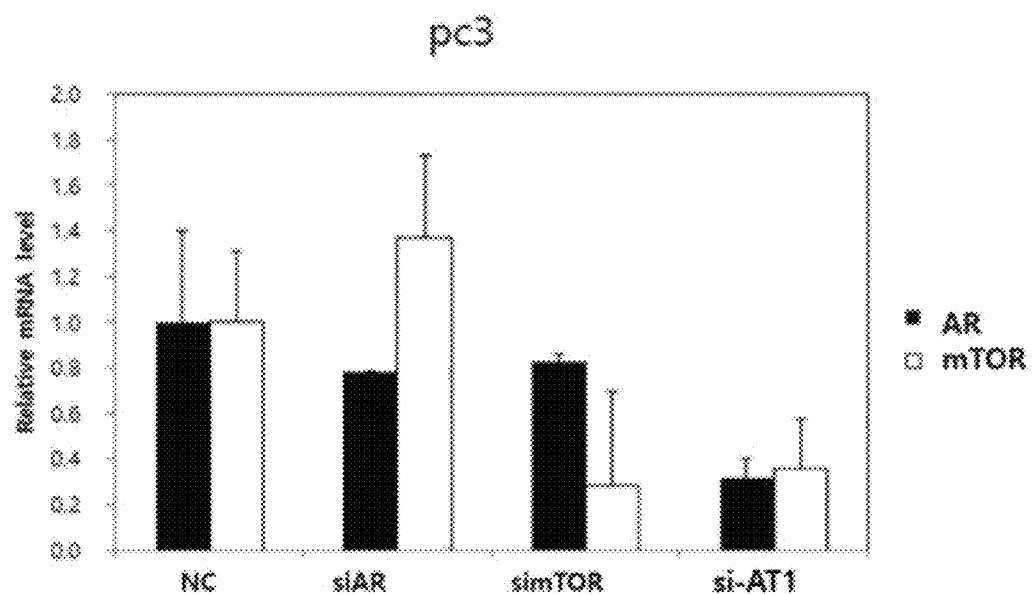
FIG. 2B is a diagram identifying the inhibitory effect of AR gene and mTOR gene expression by double target siRNA set 1 according to the present disclosure on the pc3 cell line (NC is control siRNA, siAR is siRNA for AR, simTOR is siRNA for mTOR, si-AT1 is AR and mTOR double target siRNA set 1 according to the present disclosure).

As a result, expression of both the AR and mTOR was reduced by the double target siRNA set 1 (si-AT1) according to the present disclosure in both PC3 cells and h460 cell lines. The degree of reduction was similar to or better than the effect by each siRNA. Thus, it may be seen that the double target siRNA according to the present disclosure may effectively inhibit the expression of both the AR and mTOR genes at the same time (FIG. 2A and FIG. 2B).

1-2. Identification of AR and mTOR Genes Expression Inhibitory Effect by Double Target siRNA Set 2-13 (si-AT2 to si-AT13)

The A549 cell line was used in the method described in Experimental Example 1-1 to identify the effect of inhibiting the AR and mTOR genes expression.

Figure 3:
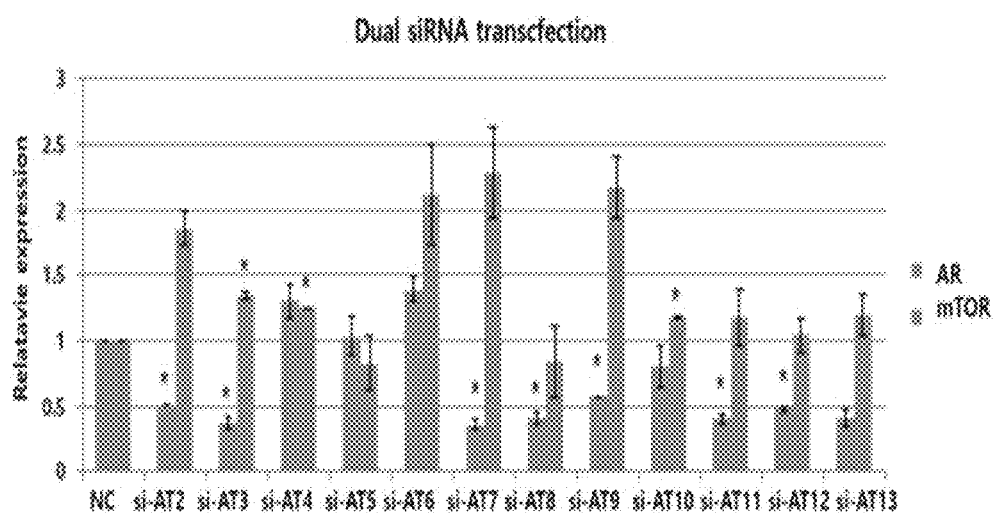
FIG. 3 is a diagram identifying the inhibitory effect of AR gene and mTOR gene expression by double target siRNA sets 2 to 13 according to the present disclosure on A549 cell line (NC is control siRNA, and si-AT2 to si-AT13 are the siRNA sets 2 to 13 according to present disclosure, respectively).

As a result, the expression of both AR and mTOR was reduced by the double target siRNA sets 2 to 13 (si-AT2 to si-AT13) according to the present disclosure in A549 cell line. It may be seen that the expression of the AR and mTOR genes may be effectively inhibited at the same time (FIG. 3).

Experimental Example 2. Identification of Cancer Cell Death Effect by Treatment with Combination of Double Target SiRNA and Anticancer Agent After incubating the DU145 cell line and the H460 cell line in 6-well plates respectively, we transfected the double target siRNA set 1 (si-AT1) according to the present disclosure thereto. Then, as 48 hours lapsed, the cells were treated with cisplatin 50 uM, etoposide 20 uM or Taxol 1 uM and were incubated for 16 hours. Thereafter, the cells were treated with 5 mg/mL MTT (Promega, Ltd.) and incubated for 4 hours, and then the medium was removed. The cells were treated with 150 μl of solubilization solution and stop solution and then were incubated at 37° C. for 4 hours. Absorbance of the reaction solution was measured at 570 nm and cell viability was calculated using the following equation.

Cell viability=(Absorbance of experiment group at 570 nm/Absorbance of control at 570 mm)×100(%)   [Equation 1]

Figure 4A:
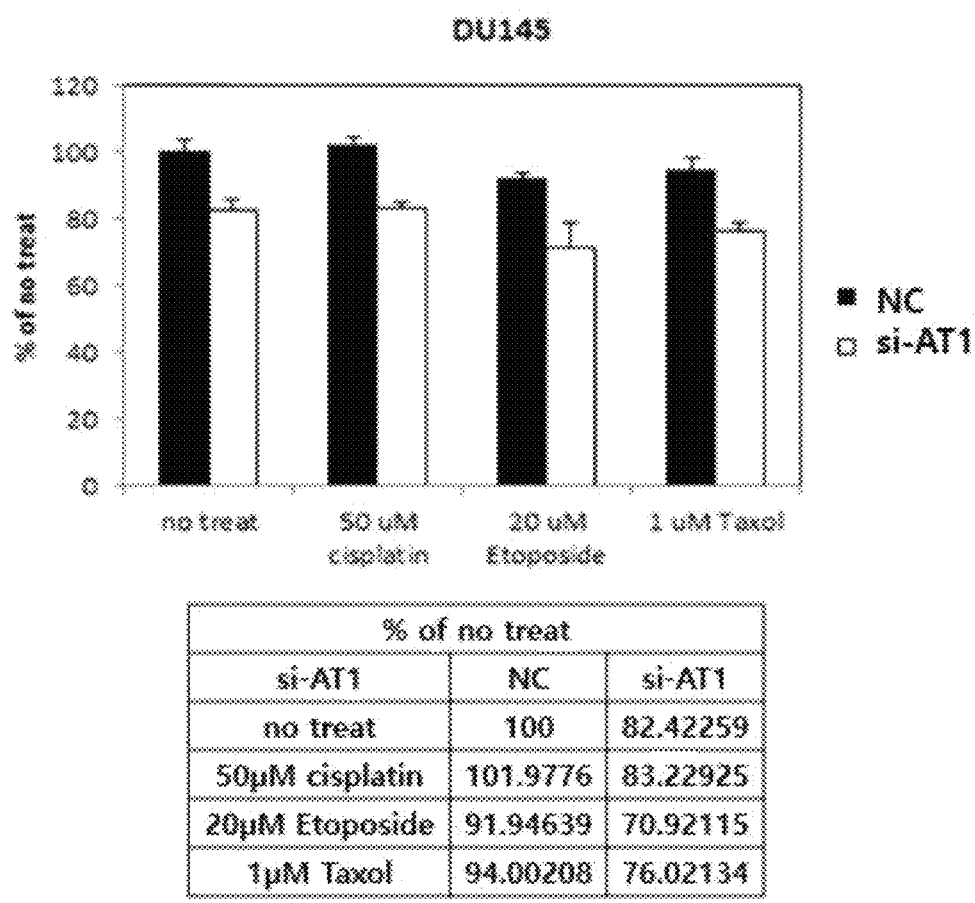
FIG. 4A is a diagram identifying effects of cancer cell death by treatment with the combination of anticancer agents and the double target siRNA set 1 on DU145 cell line (NC is control siRNA, "no treat" refers to a group as not treated with the anticancer agent, si-AT1 is AR and mTOR double target siRNA set 1 according to the present disclosure).

As a result, in DU145 cell line as the prostate cancer cell line, the double target siRNA according to the present disclosure alone caused apoptosis ("no treat" in which the anticancer agent is not applied). It was also found that the double target siRNA according to the present disclosure induced the apoptosis in the cisplatin-treated group in which apoptosis effect was not achieved. Further, treatment with the combination of the double target siRNA set 1 (si-AT1) according to the present disclosure and the etoposide and taxol having a little anticancer activity may achieve a significant improvement in the DU145 cell death (FIG. 4A).

Figure 4B:
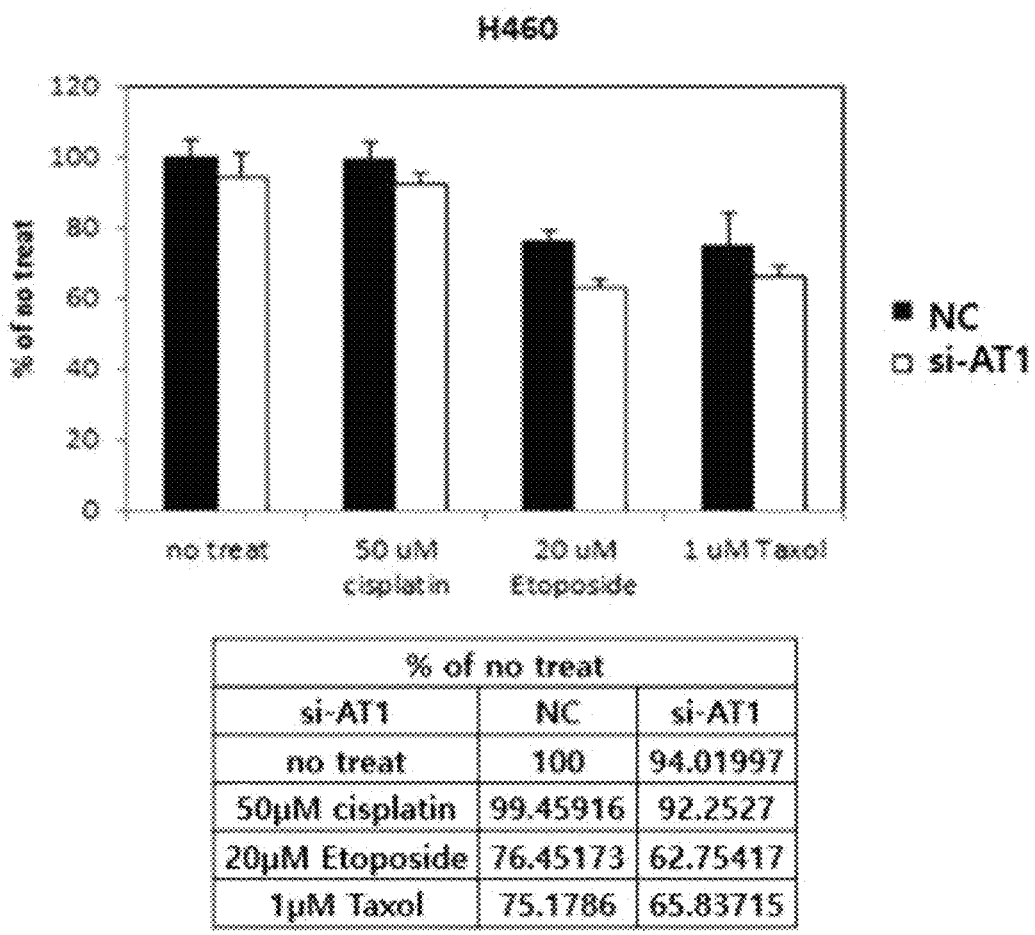
FIG. 4B is a diagram identifying the effect of cancer cell death by treatment with the combination of anticancer agents and the double target siRNA set 1 on H460 cell line (NC is control siRNA, "no treat" refers to a group as not treated with the anticancer agent, si-AT1 is AR and mTOR double target siRNA set 1 according to the present disclosure).

Further, similarly to the DU145 cell line, the double target siRNA itself showed apoptosis effect on the lung cancer cell line H460. Further, the treatment with the combination of the double target siRNA set 1 (si-AT1) according to the present disclosure and the etoposide and taxol results in significant anticancer activity on the lung cancer cell line H460 (FIG. 4B).

The invention claimed is:

1. A double-stranded siRNA molecule in which SEQ ID NO: 1 partially complementarily binds to SEQ ID NO: 2, SEQ ID NO: 3 partially complementarily binds to SEQ ID NO: 4, SEQ ID NO: 5 partially complementarily binds to SEQ ID NO: 6, SEQ ID NO: 7 partially complementarily binds to SEQ ID NO: 8, SEQ ID NO: 9 partially complementarily binds to SEQ ID NO: 10, SEQ ID NO: 11 partially complementarily binds to SEQ ID NO: 12, SEQ ID NO: 13 partially complementarily binds to SEQ ID NO: 14, SEQ ID NO: 15 partially complementarily binds to SEQ ID NO: 16, SEQ ID NO: 17 partially complementarily binds to SEQ ID NO: 18, SEQ ID NO: 19 partially complementarily binds to SEQ ID NO: 20, SEQ ID NO: 21 partially complementarily binds to SEQ ID NO: 22, SEQ ID NO: 23 partially complementarily binds to SEQ ID NO: 24, or SEQ ID NO: 25 partially complementarily binds to SEQ ID NO: 26, or a double-stranded siRNA molecule having at least 80% sequence identity with respect to each strand of the above double-stranded siRNA molecule.

2. A nucleic acid molecule which is a shRNA molecule in which SEQ ID NO: 1 partially complementarily binds to SEQ ID NO: 2, SEQ ID NO: 3 partially complementarily binds to SEQ ID NO: 4, SEQ ID NO: 5 partially complementarily binds to SEQ ID NO: 6, SEQ ID NO: 7 partially complementarily binds to SEQ ID NO: 8, SEQ ID NO: 9 partially complementarily binds to SEQ ID NO: 10, SEQ ID NO: 11 partially complementarily binds to SEQ ID NO: 12, SEQ ID NO: 13 partially complementarily binds to SEQ ID NO: 14, SEQ ID NO: 15 partially complementarily binds to SEQ ID NO: 16, SEQ ID NO: 17 partially complementarily binds to SEQ ID NO: 18, SEQ ID NO: 19 partially complementarily binds to SEQ ID NO: 20, SEQ ID NO: 21 partially complementarily binds to SEQ ID NO: 22, SEQ ID NO: 23 partially complementarily binds to SEQ ID NO: 24, or SEQ ID NO: 25 partially complementarily binds to SEQ ID NO: 26, to form a hairpin structure, a shRNA molecule having at least 80% sequence identity with respect to each SEQ ID NO of the above shRNA molecule, or a DNA molecule encoding the shRNA molecule.

3. The shRNA molecule of claim 2 which has a sequence with at least 80% sequence identity to the sequence of SEQ ID NO: 29 or SEQ ID NO: 30.

4. A recombinant expression vector including the DNA molecule of claim 2.

5. A transformed cell into which the recombinant expression vector of claim 4 has been introduced.

6. An anticancer pharmaceutical composition including the double-stranded siRNA molecule of claim 1 as an active ingredient.

7. The anticancer pharmaceutical composition of claim 6, including an additional anticancer agent.

8. A method for treating cancer, the method comprising administering a pharmaceutically effective amount of a nucleic acid molecule to a subject in need thereof, wherein the nucleic acid molecule comprises:
  i) a double-stranded siRNA or a shRNA molecule in which SEQ ID NO: 1 partially complementarily binds to SEQ ID NO: 2, or SEQ ID NO: 15 partially complementarily binds to SEQ ID NO: 16, ii) a double-stranded siRNA or shRNA molecule having at least 80% sequence identity to each of SEQ ID NOS 1 and 2, or to each of SEQ ID NOS: 15 and 16, or iii) a DNA molecule that can express at least one of the foregoing shRNA molecules.

9. The method according to claim 8, wherein the nucleic acid molecule is administered in a form of an anticancer pharmaceutical composition comprising the nucleic acid molecule as an active ingredient.

10. The method according to claim 9, wherein the anticancer pharmaceutical composition comprises an additional anticancer agent.

* * * * *